US009295849B2

(12) United States Patent
Elghazzawi et al.

(10) Patent No.: US 9,295,849 B2
(45) Date of Patent: Mar. 29, 2016

(54) MEDICAL EQUIPMENT MESSAGING

(75) Inventors: Ziad F. Elghazzawi, Newton, MA (US);
C. Shane Reid, Denver, CO (US);
Melissa M. Dascoli, Wakefield, MA (US); Andrew David Funk, Boulder, CO (US); Robert Henry Gotschall, Thornton, CO (US); Charles E. Sawyer, Jr., Sudbury, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 13/560,035

(22) Filed: Jul. 27, 2012

(65) Prior Publication Data
US 2014/0031885 A1    Jan. 30, 2014

(51) Int. Cl.
*A61N 1/39*   (2006.01)
*A61N 1/372*   (2006.01)

(52) U.S. Cl.
CPC ........ *A61N 1/37247* (2013.01); *A61N 1/37282* (2013.01); *A61N 1/3993* (2013.01)

(58) Field of Classification Search
CPC .................................................. A61N 1/3993
See application file for complete search history.

(56) References Cited

U.S. PATENT DOCUMENTS

| | | | |
|---|---|---|---|
| 5,700,281 A * | 12/1997 | Brewer et al. | 607/5 |
| 7,027,870 B2 | 4/2006 | Limousin et al. | |
| 7,728,548 B2 | 6/2010 | Daynes et al. | |
| 7,769,465 B2 * | 8/2010 | Matos | 607/60 |
| 7,840,277 B2 | 11/2010 | Matos | |
| 2003/0025602 A1 | 2/2003 | Medema et al. | |
| 2003/0212311 A1 | 11/2003 | Nova et al. | |
| 2005/0107846 A1 | 5/2005 | Sweeney | |
| 2007/0213600 A1 * | 9/2007 | John et al. | 600/300 |
| 2009/0292340 A1 * | 11/2009 | Mass et al. | 607/60 |
| 2010/0241181 A1 | 9/2010 | Savage et al. | |
| 2011/0060378 A1 * | 3/2011 | Tuysserkani | 607/5 |

OTHER PUBLICATIONS

International Search Report and Written Opinion, PCT/US2013/043353, mailed Aug. 27, 2013, 10 pages.

* cited by examiner

*Primary Examiner* — Michael Kahelin
(74) *Attorney, Agent, or Firm* — Fish & Richardson P.C.

(57) ABSTRACT

Systems and techniques for providing text-based communications from medical equipment such as automated external defibrillators (AEDs) are described herein.

34 Claims, 7 Drawing Sheets

MEDICAL EQUIPMENT MESSAGING

TECHNICAL FIELD

Systems and techniques for providing text-based communications from medical equipment such as automated external defibrillators (AEDs) are described herein.

BACKGROUND

Sudden health problems such as sudden cardiac arrest and injuries caused by accidents kill thousands of people and cause permanent injury every year. Fast and competent care can be essential to positive outcomes in such situations. For example, it is said that the chance of surviving a sudden cardiac arrest falls by ten percent for every minute in delaying effective treatment.

Emergency events like sudden cardiac arrests and accidents are generally responded to by organized emergency response units, such as ambulance or fire crews, and by laypeople who are immediately around the events so that they personally witness or offer assistance for the events.

SUMMARY

In some aspects, a method includes receiving a first signal indicative of deployment of an automated external defibrillator, sending, from the automated external defibrillator, a first text message upon receipt of the first signal indicative of deployment of the automated external defibrillator, receiving a second signal indicative of discharge of the automated external defibrillator, and sending, from the automated external defibrillator, a second text message upon receipt of the second signal indicative of discharge of the automated external defibrillator.

In some additional aspects, a method includes storing a network passcode in a memory associated with the automated external defibrillator, detecting deployment of the automated external defibrillator, upon detection of deployment, establishing a connection with a secured wireless network by accessing stored passcode information for the secured wireless network, and sending one or more text messages, from the automated external defibrillator via the secured wireless network.

In some additional aspects, a method includes performing, by a self-test unit in an automated external defibrillator, a self-test of the automated external defibrillator at regular time-based intervals and sending, from the automated external defibrillator to a server, one or more text messages including information associated with results of the self-test.

Other embodiments of these aspects include corresponding computer systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

Other features and advantages of the invention will be apparent from the drawings, detailed description, and claims.

DETAILED DESCRIPTION

Described herein are systems and techniques for transmitting text messages from a rescue scene to an emergency response dispatch center or medical equipment management center. In general, text messaging is the exchange of brief written text messages between two or more devices over a phone network. Text messaging can be used to provide communications between a piece of medical equipment such as an automated external defibrillator (AED) and an emergency response dispatch center as a substitute for voice calls in situations where voice communication is impossible or undesirable.

In some examples, medical equipment, such as an automated external defibrillator (AED), is configured to establish a wireless connection with a wireless network to enable the medical equipment to send (and optionally receive) text-based messages such as short message service (SMS) or multi-media message service (MMS) messages. For example, the medical equipment can be configured to establish a wireless data connection over a Wi-Fi network and send text messages to an emergency response center (e.g., a 911 center) automatically based on deployment or activation of the medical equipment.

In some examples, described herein are systems and techniques for transmitting text messages from medical equipment, such as an automated external defibrillator (AED), to a medical equipment management system. More particularly, the medical equipment is configured to establish a wireless connection with a wireless network to enable the medical equipment to send (and optionally receive) messages to a remotely located medical equipment management system. For example, the medical equipment can be configured to send text messages to the medical equipment management system automatically based on self-test routines executed on the medical equipment.

In some examples, the medical equipment can include a cellular modem for sending/receiving of text messages. In some additional examples, the medical equipment can be configured to establish a wireless data connection over a Wi-Fi network and send text messages to the medical equipment management system and/or emergency response center via the Wi-Fi network. In some examples, in order to establish the connection with a secured Wi-Fi network which requires a passcode for access, a passcode for the network can be stored in a memory associated with the medical equipment. For example, during an initial install or configuration of the medical equipment, the network passcode can be provided and stored in a memory associated with the medical equipment. When the medical equipment determines that a text message should be sent (e.g., upon deployment, upon completion of a self-test routine), the medical equipment can establish a connection with the secured wireless network by accessing stored passcode information for the secured wireless network. Thus, in some examples, the medical equipment can send and receive text messages via a secured wireless network.

Figure 1:
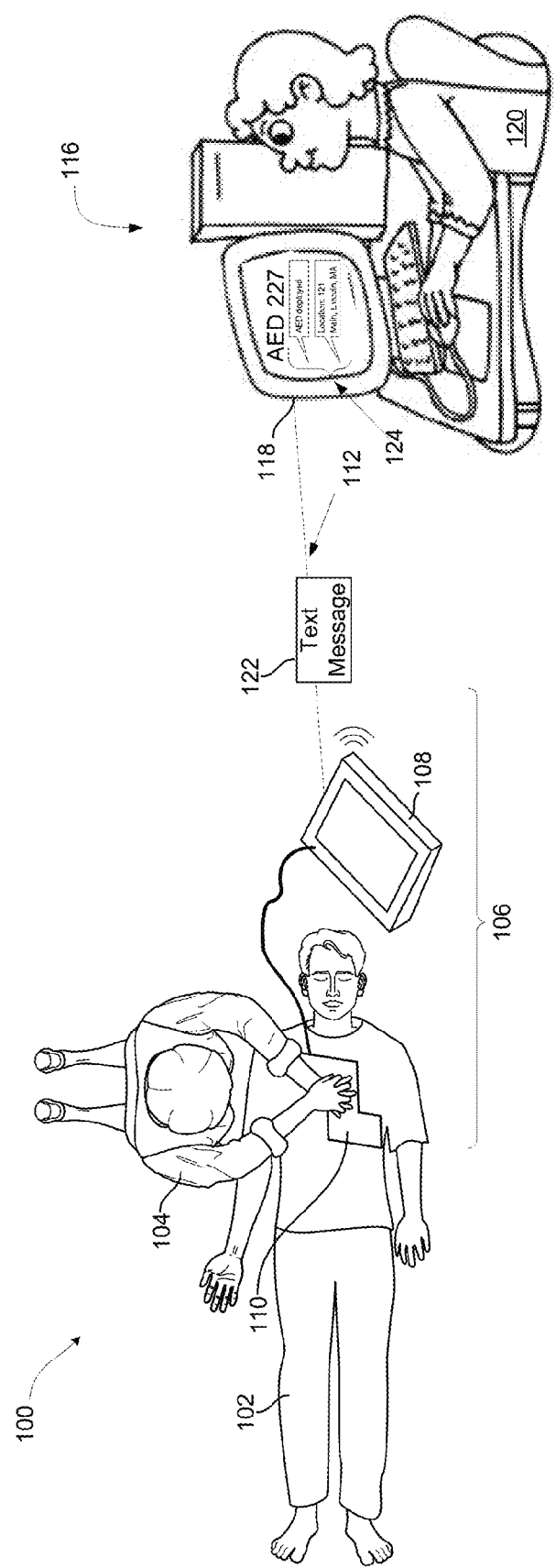
FIG. 1 is a schematic diagram of an exemplary system for responding to an emergency medical condition.

Referring to FIG. 1, at a rescue scene 100, a caregiver 104 performs cardiopulmonary resuscitation (CPR) on a subject 102. An electronic defibrillating system 106 including a defibrillator, such as an automated external defibrillator (AED) 108, a professional defibrillator, or another type of defibrillating apparatus, instructs the caregiver 104 in performing CPR and provides defibrillation as needed via external electrode pads 110. The subject may be, for instance, an individual who has apparently undergone sudden cardiac arrest. The caregiver 104 may be, for instance, a civilian responder with limited or no training in lifesaving techniques; a first responder, such as an emergency medical technician (EMT), police officer, or firefighter; or a medical professional, such as a physician or nurse. The caregiver 104 may be acting alone or may be acting with assistance from one or more other caregivers, such as a partner EMT.

The defibrillating system 106 is connected via a communication channel 112 to an emergency response center 116, such as a 911 call center, a police dispatch, an ambulance dispatch, a fire department, or another emergency response center. In some examples, the communication channel 112 can be a short-range wireless communication channel, such as a Bluetooth or WiFi connection, that is connected to a hardwired communication channel. The communication channel 112 can support the delivery of text messages 122 between the defibrillating system 106 and the emergency response center 116. The text messages from the defibrillating system 106 are displayed on a display 118 (e.g., a computer monitor, television, mobile communication device, or other display) at the emergency response center 116 (e.g., displayed messages 124), enabling a responder 120 (e.g., a dispatcher) to receive information from the defibrillating system 106. In some embodiments, the defibrillating system 106 can send information about its deployment state such as when the device is turned on or when the device delivers a defibrillation shock. In some additional embodiments, the defibrillating system 106 can also monitor the subject 102 during treatment and transmit real-time subject monitoring data to the emergency response center 116 via text message.

In some examples, the defibrillating system 106 can send a text message to the emergency response 116 center automatically upon the occurrence of certain events, such as deployment of the defibrillating system 106. Additionally, in some examples, the defibrillating system 106 can send user generated text messages such as messages input by caregiver 104 and display text messages received from the emergency response center 116 on a display unit of the defibrillating system 106, or in associated device.

Figure 2A:
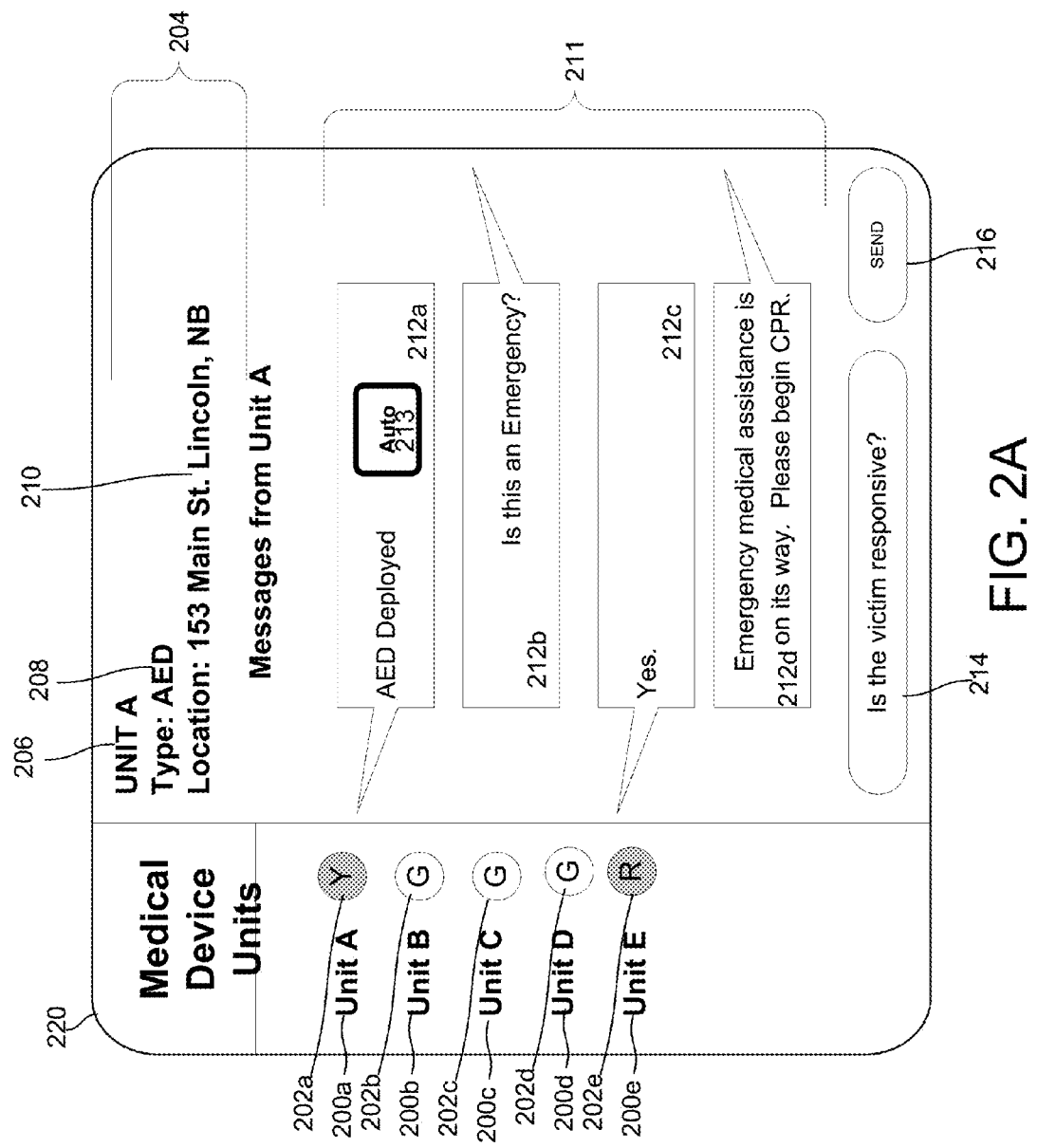
FIGS. 2A, 2B, and 2C are exemplary screen shots for displaying text-based updates from medical equipment.

FIG. 2A shows an exemplary user interface 220 at the emergency response center 116 that includes communications between the defibrillating system 106 and an individual 120 at the emergency response center. User interface 220 includes a portion 211 configured to display text messages between the defibrillating system 106 and the emergency response center 116. In the example of FIG. 2, these messages include both auto generated messages from the defibrillating system 106 such as message 212a that is sent from the defibrillating system 106 upon activation of the defibrillating system 106 and user generated messages sent from the defibrillating system 106 such as message 212c. Auto-generated messages (e.g., messages automatically generated and sent by the defibrillator) can be displayed with visual indicia 213 that indicates that the message was automatically sent. The messages in portion 211 also include messages sent from an individual at the emergency response center to the defibrillating system 106 such as messages 212b and 212d. Thus, text-based communications are provided between the defibrillating system 106 and the emergency response center. User interface 220 also includes a message input box 214, and a control 216 for sending the message to the medical device unit.

User interface 220 also includes a portion 204 that displays information about the defibrillating system 106, which is sending and receiving the messages displayed in portion 211. This information can include a unit name 206, a unit type 208 which identifies the make and model of the defibrillating system 106, and a location 210. The location can be a location determined by accessing a stored database of location information, a location provided by the defibrillating system 106 based on information stored in the defibrillating system 106, or a location provided by the defibrillating system 106 unit based on GPS location data.

User interface 220 also includes a control area for selecting different defibrillating systems. Selection of a different system displays communications between the selected defibrillating system and the emergency response center in area 211. The control area can include a unit identifier such as unit identifiers 200a-e and a status indicator such as status indicators 202a-e. The status indicators can indicate when a text message has been received from the associated the defibrillating system. The status indicators can be displayed as color-coded icons associated with each piece of medical equipment where the color coding is indicative of the status. For example as shown in FIG. 2A, the entries in the status column can be color-coded to indicate whether a new/unread message has been received from the associated defibrillating system. In one particular example, a red color coding of the icon could be representative of equipment for which a new text message that is the first text message in a conversation has been received, a yellow color coding can be representative of equipment for which a new message has been received in an ongoing series of text messages, and a green color coding could be representative of equipment for which no text messages have been received within a particular time period. In the particular example shown in FIG. 2A, device 200a has a status indicator 202a indicating that a new message has been received in an ongoing conversation and device 200e has a status indicator 202e indicating that a new message has been received which is the first message in a new conversation.

Figure 2B:
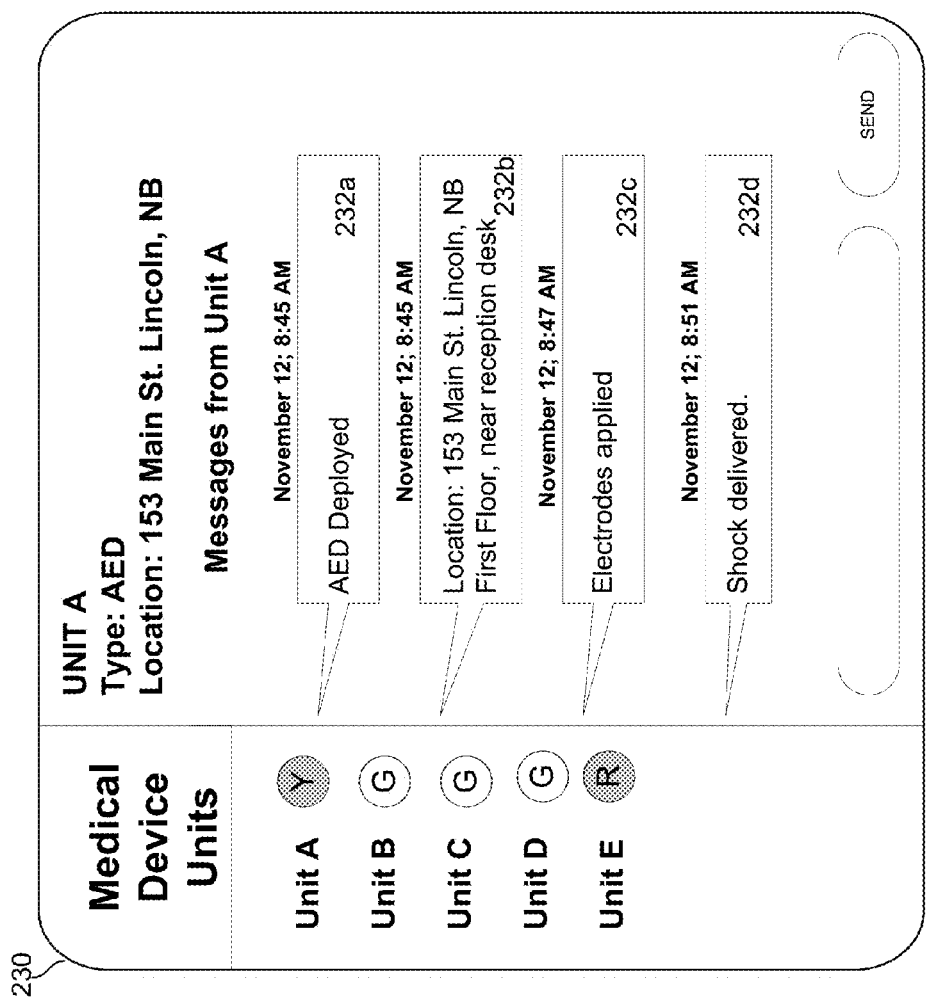

In some examples, as shown in FIG. 2B, a defibrillation device such as a defibrillation unit 106 in FIG. 1 can provide automatically generated text messages (e.g., messages 232a-d) to the emergency response center (or to another device such as a handheld device or a mobile phone used by an EMT or computing device in an ambulance). These messages can be automatically generated based on the occurrence of certain events on defibrillation unit. For example, messages can include a deployment message 232a sent to the emergency response center when the defibrillation unit is deployed, an application message 232c sent when electrodes have been applied, a defibrillation message 232d sent when a defibrillation shock has been administered, or upon other occurrences. Additionally, the automatically generated messages can include a location message 232b that provides a current location for the defibrillation unit sending the text message. Such messages can allow the emergency response center to be informed of the status of an ongoing rescue without requiring the rescuer to interrupt his or her administration of CPR or performance of other activities. Additionally, automatic generation and transmission of a text message upon deployment of medical equipment such as a defibrillation unit can reduce the time between when a rescue begins and when the emergency response center is notified. For example, rather than notification to the emergency response center occurring upon the rescuer initiating a 911 call, such notification can automatically occur whenever the defibrillation unit is deployed.

Figure 2C:
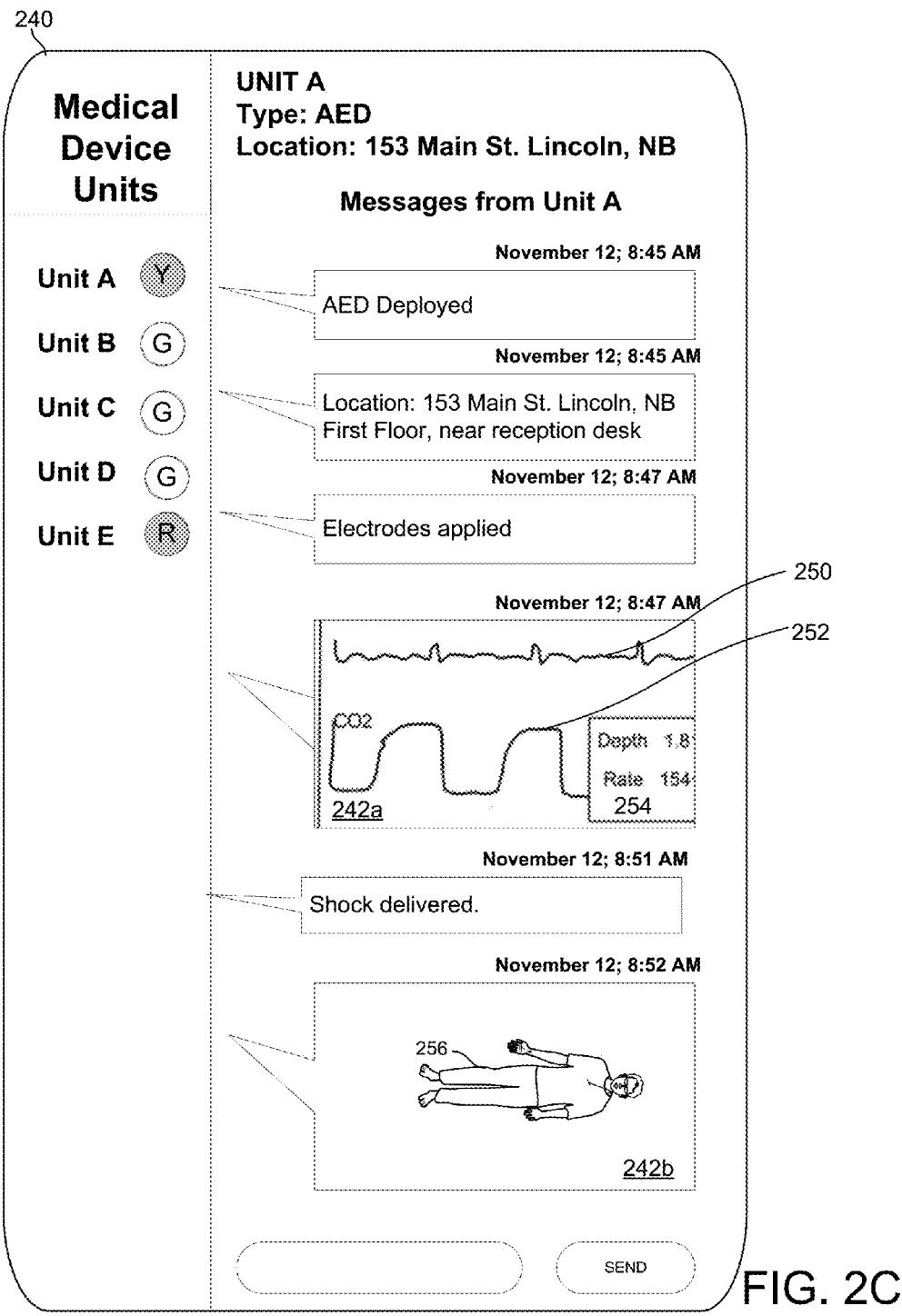

In some examples, the defibrillating system 106 can additionally monitor the subject 102 during treatment and collect real-time subject monitoring data. As shown in FIG. 2C, this monitoring data can be transmitted to the emergency response center via text message either as a screen capture using a MMS message (e.g., as shown in message 242a) or as text-based information (not shown). For instance, signals such as an ECG waveform (e.g., signal 250), an $SpO_2$ level, a blood pressure, $CO_2$ (e.g., signal 252), a measure of cardiac output, or a measure of heart rate may be monitored and summary information can be sent to the emergency response center via text message. Alternatively or additionally, compression parameters, such as a sternal motion signal, a compression rate, a compression depth, or another measurement of compression, may be monitored and sent to the emergency response center via text message (e.g., as shown in box 254). Some or all of these types of subject monitoring data may be transmitted from the defibrillation unit to the emergency response center 116 via text messages.

In some additional examples, as shown in FIG. 2C, the defibrillating system 106 and additionally include a camera (not shown) for capturing image information from the rescue scene. The captured image information can be sent to the emergency response center via text message. For example, a text message, such as message 242b can include a photograph 256 or other image information, such as video information, obtained by the camera associated with the defibrillating system. Providing such image information can be beneficial in allowing the emergency response center and/or a potential responder to remotely assess the situation, deploy the appropriate responders, and/or provide instructions to a rescuer.

Figure 3:
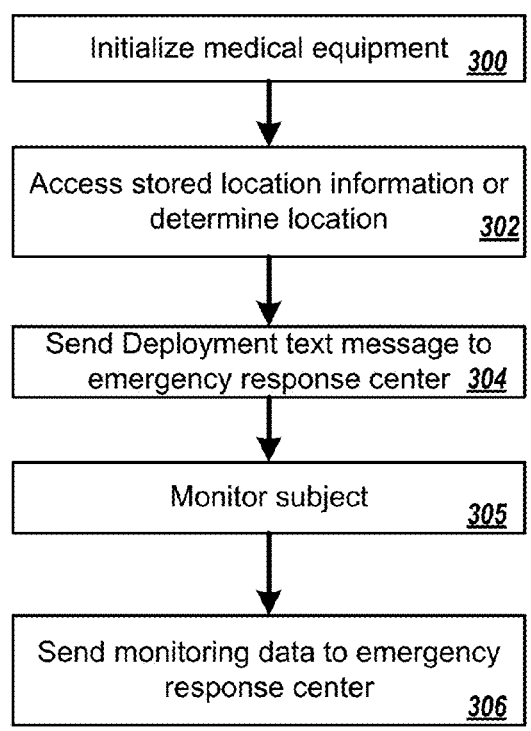
FIG. 3 is a flow chart of a process for sending text-based updates from medical equipment according to an example embodiment of the invention.

As noted above, in some examples, the defibrillation unit can provide location information automatically via text message (e.g., text message 232b in FIG. 2B). FIG. 3 shows an exemplary process for sending text-based updates from the defibrillation unit. The process begins with the initialization of the defibrillation unit (300). Upon initialization, the defibrillation unit accesses stored location information or determines the location of the defibrillation unit (302). For example, the location information can be stored in a memory associated with the defibrillation unit and accessed at the time of initialization. In another example, the defibrillation unit can include a GPS device which can be used to determine a current location for the defibrillation unit. The defibrillation unit sends a text message (e.g., an SMS or MMS message) to an emergency response center, indicating the defibrillation unit has been deployed (304). This text message includes information about the location of the defibrillation unit. In some additional examples, two separate text messages can be sent with a first indicating that the defibrillation unit has been deployed and a second indicating the current location of the defibrillation unit. The defibrillation unit monitors the subject during treatment and collects real-time subject monitoring data, such as the monitoring data described above (305). A subset of the monitored subject data is sent to the emergency response center in the form of a text message (306).

While the examples described above in relation to FIGS. 1-3 describe sending text messages between defibrillation units and an emergency response center, text messages can be sent from a variety of types of emergency medical equipment, such as medical monitors to the emergency response center.

While the examples described above in relation to FIGS. 1-3 describe sending text messages between emergency medical equipment such as AEDs and an emergency response center, text messages can be sent from emergency medical equipment to a variety of remotely located devices and systems. For example, the messages described above as being sent to the emergency response center could additionally or alternatively be sent to a mobile phone of a responder, such as an EMS responder, to a hospital, to a computing device located in an ambulance, or to other individuals who may be equipped to respond to the emergency situation.

In some additional examples, text messages can be used to assist in maintaining medical equipment such as defibrillation units. In order for a defibrillator to be useful during a medical emergency, the defibrillator must be charged and functional when the device is needed. In order to ensure the defibrillators are functional, regular servicing is needed. For example, batteries must be replaced when they no longer store adequate charge to power the defibrillator, electrodes may need to be replaced to ensure the electrodes will function appropriately, and the like. As such, after defibrillator is purchased and installed regular servicing is provided to ensure that the defibrillator will be available and functional when needed. In some examples, the defibrillation unit can send text messages to convey a status of the defibrillation unit. These messages can assist a user to provide servicing to the defibrillation units when needed. For example, if a battery in the defibrillation unit has a low level of charge, the defibrillation unit can send a text message to a servicing center and based on this text message, the servicing center can deploy an individual to replace the battery in the defibrillation unit.

Figure 4:
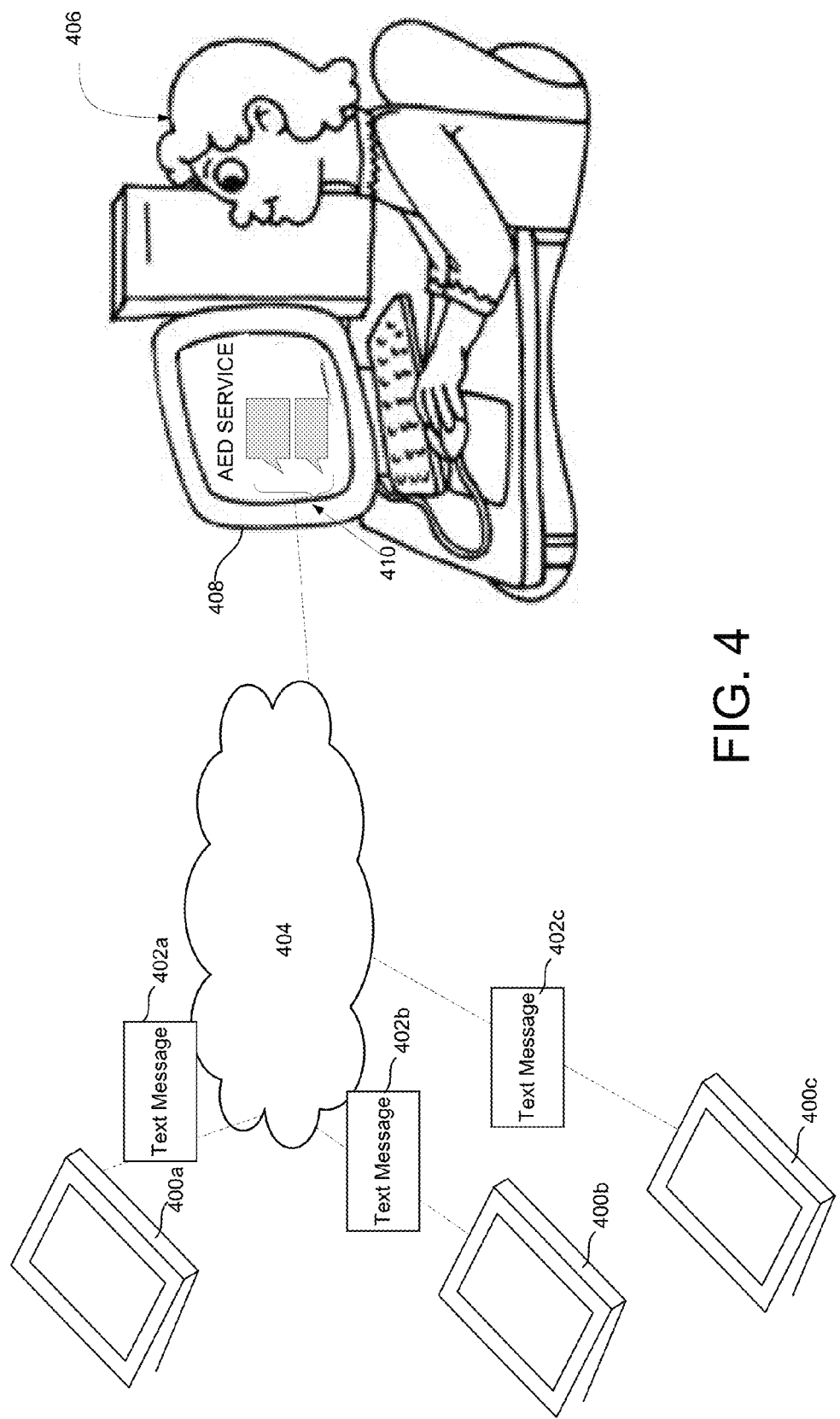
FIG. 4 is a schematic diagram of a system for managing medical equipment according to an example embodiment of the invention.

For example, as shown in FIG. 4, defibrillation units such as AEDs 400a, 400b, and 400c can send text messages (e.g., text messages 402a-c) to a service center 408. The text messages can be displayed on a user interface (e.g., as messages 410) for an individual 406 at the service center to review and take appropriate actions based on the received text messages. The text messages 402a-c can be sent to the service center 408 over the Internet 404 and/or over a cellular communication channel.

Figure 5:
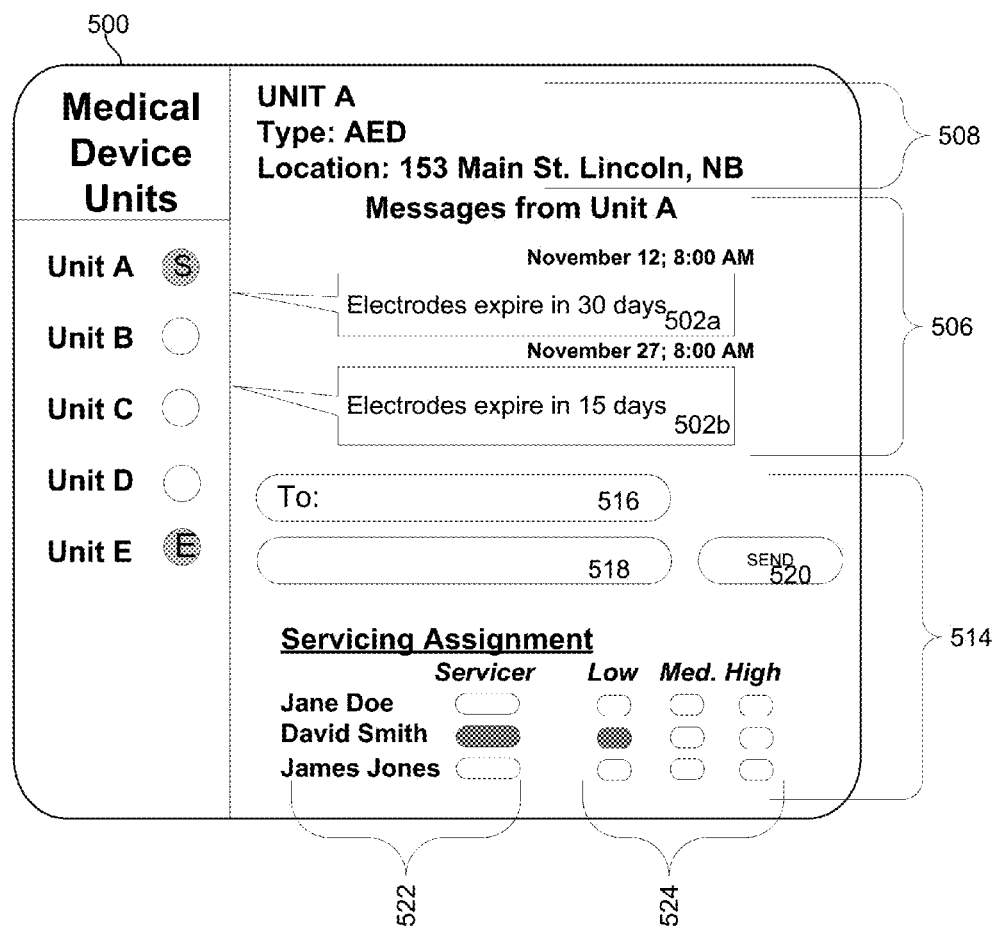
FIG. 5 is an exemplary screen shot for displaying text-based updates including status information for medical equipment.

FIG. 5 shows an exemplary screen shot for providing information about the status of defibrillation units to an administrator of the defibrillation units.

User interface 500 includes a portion 506 configured to display text messages between the defibrillation unit and an individual at the service center. These messages can include automatically generated messages from the defibrillation unit such as messages that convey status information about the defibrillation unit.

User interface 500 also includes a message assignment and forwarding portion 514. The message assignment and forwarding portion 514 enables a user at the service center to forward the text message from the defibrillation unit to another individual and/or to assign servicing to a particular individual. For example, upon receipt of the text message from a particular defibrillation unit, a user could forward the text message to another individual such that that individual could perform the needed servicing. The user at the service center could forward the message by entering an identifier/username for the individual to forward the message to in box 516, and optionally entering an additional message in box 518. The message from the defibrillator and the additional message from the user at the service center (if provided) can be forwarded to the individual identified in box 516 by selection of the send button 520.

In some additional examples, servicing can be assigned by selection of an individual from a list of individuals 522 available to perform the servicing. For example, a servicing company could maintain a list of individuals who perform needed servicing of the medical devices and particular tasks could be assigned to those individuals by selecting the individual. Additionally, user interface 500 allows a user at the service center to assign urgency to the servicing by selecting and associated urgency box in section 524. In the example shown in user interface 500, the user at the service center has assigned servicing of the 'unit A' to David Smith by selecting the input associated with David Smith and assigned an urgency of "low" by selecting associated control. Upon making the selections, a message is sent to the selected individual providing information about the needed servicing.

User interface 500 also includes a portion 508 that displays information about the defibrillation unit, which is sending and receiving the messages displayed in portion 506. This information can include a unit name, a unit type which identifies the make and model of the defibrillation unit, and a location. The location can be a location determined by accessing a store database of location information, a location provided by the defibrillation unit based on information stored in the medical device unit, or a location provided by the defibrillation unit based on GPS location data.

User interface 500 also includes a control area for selecting defibrillation units. Selection of a different unit displays communications between the selected defibrillation unit and the service center in area 506. The control area can include a unit identifier such and a status indicator. The status indicators can indicate when a text message has been received from the associated defibrillation unit. The status indicators can be displayed as color-coded icons associated with each piece of medical equipment where the color coding is indicative of the status. For example as shown in FIG. 5, the entries in the status column can be color-coded to indicate whether a new/unread message has been received from the associated defibrillation unit. In one particular example, a red color coding of the icon could be representative of equipment for which a new text message indicating an error has been received, a yellow color coding can be representative of equipment for which a new message has been received indicating expiration of a component or other routine servicing is needed, and a green color coding could be representative of equipment for which no text messages have been received within a particular time period. In the particular example shown in FIG. 5, unit 'A' has a status indicator indicating that servicing is needed (e.g., that the electrodes will expire in 15 days) and unit 'E' has a status indicator indicating that an error message has been received.

In some examples, a defibrillator can include a self-test unit configured to perform self-tests at regular time-based intervals. The results of the self-test can be sent to the servicing center via text message. Thus, if a problem is identified by the self-test, details are provided to the servicing center. Further, because self-tests are scheduled to occur at regular time intervals, the servicing center can identify failures in devices based on the lack of an expected message. For example, if a defibrillation unit is scheduled to perform a self-test monthly, and the results are not received, then the servicing center can identify the defibrillation unit as potentially having a problem that is prohibiting performance of the self-test (e.g., a battery with inadequate charge).

While the examples described above in relation to FIGS. 4-5 describe sending text messages between defibrillation units and a service center, text messages can be sent from a variety of types of medical equipment, such as medical monitor equipment to the service center.

A number of embodiments have been described. Nevertheless, it will be understood that various modifications may be made without departing from the spirit and scope of the invention. For example, much of this document has been described with respect to defibrillation units, but other types of devices may be employed.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims. Many other implementations of the invention other than those described above are within the invention, which is defined by the following claims.

What is claimed is:

1. A method, comprising:
   during configuration of an automated external defibrillator configured for two-way text-based communications, storing, in a memory associated with the automated external defibrillator, an identifier of a secured wireless network and a network passcode for the secured wireless network, the network passcode comprising a network passcode required to gain access to the secured wireless network;
   receiving a first signal indicative of deployment of the automated external defibrillator;
   upon detection of deployment of the automated external defibrillator, establishing a connection with the secured wireless network by accessing the stored network passcode for the secured wireless network;
   automatically sending, from the automated external defibrillator, via the secured wireless network, a first text message upon receipt of the first signal indicative of deployment of the automated external defibrillator;
   receiving a second signal indicative of one or more electrodes of the deployed automated external defibrillator being applied;
   automatically sending, from the automated external defibrillator, via the secured wireless network, a second text message upon receipt of the second signal indicative of the one or more electrodes being applied;
   receiving a third signal indicative of discharge of the automated external defibrillator;
   automatically sending, from the automated external defibrillator, via the secured wireless network, a third text message upon receipt of the third signal indicative of discharge of the automated external defibrillator; and
   receiving, from an emergency response entity, via the secured wireless network, a text message responsive to at least one of the first, second, and third text message.

2. The method of claim 1, further comprising:
   determining a location associated with the automated external defibrillator; and
   wherein sending the first text message includes sending a text message that includes the location information associated with the automated external defibrillator.

3. The method of claim 2, wherein determining the location comprises accessing location information stored on a memory associated with the automated external defibrillator.

4. The method of claim 2, wherein determining the location comprises receiving location information from a global positioning unit included in the automated external defibrillator.

5. The method of claim 1, further comprising:
   receiving image information from a camera associated with the automated external defibrillator, and sending a text message that includes the image information.

6. The method of claim 1, wherein one or more of the first, second, and third text messages comprise short message service messages.

7. The method of claim 1, wherein one or more of the first, second, and third text messages comprise multi-media message service messages.

8. The method of claim 1, wherein the received text message includes a question directed to a user of the automated external defibrillator.

9. The method of claim 8, comprising sending, from the automated external defibrillator, via the secured wireless network, a user generated text message responsive to the received text message.

10. The method of claim 1, wherein the received text message includes information related to a status of incoming emergency medical assistance.

11. The method of claim 10, wherein the received text message includes an indication that emergency medical assistance is en route to the automated external defibrillator.

12. The method of claim 1, wherein the received text message includes a treatment instruction.

13. The method of claim 12, wherein the received text message includes an instruction to commence CPR.

14. An automated external defibrillator configured for two-way text-based communications, the automated external defibrillator comprising:
   a computing device configured to determine deployment of the automated external defibrillator and determine discharge of the automated external defibrillator;
   a memory configured to store an identifier of a secured wireless network and a network passcode for the secured wireless network, the network passcode comprising a network passcode required to gain access to the secured wireless network; and
   a communication unit configured to:
      establish a connection with the secured wireless network by accessing the stored network passcode for the secured wireless network;
      automatically send, from the automated external defibrillator, via the secured wireless network, a first text message upon deployment of the automated external defibrillator, automatically send a second text message upon one or more electrodes of the automated defibrillator being applied, and automatically send a third text message upon discharge of the automated external defibrillator; and
      receive, from an emergency response entity, via the secured wireless network, a text message responsive to at least one of the first, second, and third text message.

15. The automated external defibrillator of claim 14, further comprising:
   a global positioning unit configured to determine a location associated with the automated external defibrillator; and
   wherein the communication unit is further configured to send a text message that includes the location information associated with the automated external defibrillator.

16. The automated external defibrillator of claim 14, further comprising:
   a memory configured to store a location associated with the automated external defibrillator; and
   wherein the communication unit is further configured to send a text message that includes the location information associated with the automated external defibrillator.

17. The automated external defibrillator of claim 14, further comprising:
   a camera configured to receiving image information, wherein the communication unit is further configured to send a text message that includes the image information.

18. The automated external defibrillator of claim 14 wherein one or more of the first, second, and third text messages comprise short message service messages or multi-media message service messages.

19. The automated external defibrillator of claim 14, wherein the received text message includes a question directed to a user of the automated external defibrillator.

20. The automated external defibrillator of claim 19, wherein the communication unit is configured to send, from the automated external defibrillator, via the secured wireless network, a user generated text message responsive to the received text message.

21. The automated external defibrillator of claim 14, wherein the received text message includes information related to a status of incoming emergency medical assistance.

22. The automated external defibrillator of claim 21, wherein the received text message includes an indication that emergency medical assistance is en route to the automated external defibrillator.

23. The automated external defibrillator of claim 14, wherein the received text message includes a treatment instruction.

24. The automated external defibrillator of claim 23, wherein the received text message includes an instruction to commence CPR.

25. A method comprising:
   during configuration of an automated external defibrillator configured for two-way text-based communications, storing, in a memory associated with the automated external defibrillator, an identifier of a secured wireless network and a network passcode for the secured wireless network, the network passcode comprising a network passcode required to gain access to the secured wireless network;
   detecting deployment of the automated external defibrillator;
   upon detection of deployment, establishing a connection with the secured wireless network by accessing the stored network passcode for the secured wireless network;
   automatically sending one or more multi-media message service messages, from the automated external defibrillator, via the secured wireless network;
   upon detecting one or more electrodes of the automated external defibrillator being applied, sending one or more multi-media message service messages, from the automated external defibrillator, via the secured wireless network;
   upon detecting discharge of the automated external defibrillator, sending one or more multi-media message service messages, from the automated external defibrillator, via the secured wireless network; and
   receiving, from an emergency response entity, via the secured wireless network, one or more multi-media message service messages responsive to at least one of the detected deployment, the detected one or more electrodes being applied, and the detected discharge of the automated external defibrillator.

26. The method of claim 25, wherein sending one or more multi-media message service messages, from the automated external defibrillator via the secured wireless network comprises:

sending, from the automated external defibrillator, a first multi-media message service message upon receipt of a first signal indicative of deployment of the automated external defibrillator;

sending, from the automated external defibrillator, a second multi-media message service message upon receipt of a second signal indicative of one or more electrodes of the deployed automated external defibrillator being applied; and sending, from the automated external defibrillator, a third multi-media message service message upon receipt of a third signal indicative of discharge of the automated external defibrillator.

27. The method of claim 25, further comprising:

determining a location associated with the automated external defibrillator; and wherein sending the one or more multi-media message service messages includes sending a multi-media message service message that includes the location information associated with the automated external defibrillator.

28. The method of claim 25, further comprising:

receiving image information from a camera associated with the automated external defibrillator, and wherein sending the one or more multi-media message service messages comprises sending a multi-media message service message that includes the image information.

29. The method of claim 25, wherein the received one or more multi-media message service message includes a question directed to a user of the automated external defibrillator.

30. The method of claim 29, comprising sending, from the automated external defibrillator, via the secured wireless network, a user generated text message responsive to the received one or more multi-media message service message.

31. The method of claim 25, wherein the received one or more multi-media message service message includes information related to a status of incoming emergency medical assistance.

32. The method of claim 31, wherein the received one or more multi-media message service message includes an indication that emergency medical assistance is en route to the automated external defibrillator.

33. The method of claim 25, wherein the received one or more multi-media message service message includes a treatment instruction.

34. The method of claim 33, wherein the received one or more multi-media message service message includes an instruction to commence CPR.

* * * * *